(12) United States Patent
Lee

(10) Patent No.: US 9,259,561 B2
(45) Date of Patent: Feb. 16, 2016

(54) TATTOOING APPARATUS CAPABLE OF ADJUSTING THE CONCENTRATION OF PIGMENT FLUID FOR TATTOOS OR SEMI-PERMANENT TATTOOS

(75) Inventor: Jong-Dae Lee, Seocho-gu (KR)

(73) Assignee: Bomtech Electronics Co., Ltd. (KR)

( * ) Notice: Subject to any disclaimer, the term of this patent is extended or adjusted under 35 U.S.C. 154(b) by 1064 days.

(21) Appl. No.: 13/383,127

(22) PCT Filed: Jul. 13, 2010

(86) PCT No.: PCT/KR2010/004541
§ 371 (c)(1),
(2), (4) Date: Jan. 9, 2012

(87) PCT Pub. No.: WO2011/008004
PCT Pub. Date: Jan. 20, 2011

(65) Prior Publication Data
US 2012/0271335 A1    Oct. 25, 2012

(30) Foreign Application Priority Data

Jul. 14, 2009  (KR) ................. 10-2009-0064033

(51) Int. Cl.
*B43K 5/00*    (2006.01)
*A61M 37/00*   (2006.01)
*A61M 5/46*    (2006.01)

(52) U.S. Cl.
CPC ........... *A61M 37/0084* (2013.01); *A61M 5/46* (2013.01)

(58) Field of Classification Search
CPC ........... A61B 17/34; A61B 17/3417; A61B 17/3496; A61B 2019/481; A61B 17/0049; A61M 37/0076; A61M 37/00; A61M 37/0084; A61M 5/145; A61M 5/155; A61M 5/48; A61M 5/482; A61M 5/484; A61M 5/486; A61M 5/488; A61M 5/46; A61M 5/3298; A61M 3/0216; A61M 3/0233; A61M 3/0237; A61M 3/0241; A61M 37/0015; A61M 37/0092; A45D 44/00; A45D 35/46; A45D 85/00; B43K 5/00; B26F 1/34
USPC ................... 81/9.2, 9.22; 606/185–186, 116; 604/191, 236, 173, 192, 218, 232
See application file for complete search history.

(56) References Cited

U.S. PATENT DOCUMENTS

| | | | | |
|---|---|---|---|---|
| 4,392,493 | A | * | 7/1983 | Niemeijer ................ 606/116 |
| 4,671,277 | A |   | 6/1987 | Beuchat |
| 4,796,624 | A | * | 1/1989 | Trott et al. ................ 606/185 |
| 5,471,102 | A | * | 11/1995 | Becker et al. ................ 310/50 |
| 5,961,495 | A | * | 10/1999 | Walters ............ A61M 5/31553 604/111 |
| 6,264,637 | B1 | * | 7/2001 | Hogan ............... A01K 11/00 604/191 |
| 6,345,553 | B1 |   | 2/2002 | Adler et al. |

(Continued)

FOREIGN PATENT DOCUMENTS

| | | |
|---|---|---|
| EP | 1524201 A1 | 4/2005 |
| KR | 100789398 B1 | 12/2007 |

*Primary Examiner* — Monica Carter
*Assistant Examiner* — Melanie Alexander
(74) *Attorney, Agent, or Firm* — Blank Rome LLP

(57) ABSTRACT

A tattooing apparatus, which have a tattoo needle traveling back and forth to a skin to allow a staining solution for tattoo contained in the apparatus to penetrate into the skin and thus to get a tattoo and which can adjust a concentration of the staining solution for tattoo, is disclosed. The tattooing apparatus includes a chamber pressure adjusting member to adjust a degree of opening and closing an inlet of a storing chamber in which the staining solution for tattoo is stored, thus to adjust a pressure in the storing chamber.

18 Claims, 11 Drawing Sheets

(56) References Cited

U.S. PATENT DOCUMENTS

| | | |
|---|---|---|
| 6,505,530 B2 | 1/2003 | Adler et al. |
| 2002/0069726 A1 | 6/2002 | Adler et al. |
| 2003/0171767 A1* | 9/2003 | Koplen .............. A61M 37/0076 606/185 |
| 2006/0106362 A1* | 5/2006 | Pass ........................ A61M 5/30 604/504 |
| 2006/0173439 A1* | 8/2006 | Thorne ............. A61M 5/14244 604/506 |
| 2006/0276755 A1* | 12/2006 | Sullivan .............. A61M 5/2448 604/187 |
| 2007/0235083 A1* | 10/2007 | Dlugos ................. A61F 5/0003 137/223 |
| 2008/0103564 A1* | 5/2008 | Burkinshaw ..... A61B 17/00491 607/96 |
| 2008/0269694 A1* | 10/2008 | Pieringer .............. A61B 19/54 604/218 |
| 2010/0191268 A1 | 7/2010 | Lee |

\* cited by examiner

TATTOOING APPARATUS CAPABLE OF ADJUSTING THE CONCENTRATION OF PIGMENT FLUID FOR TATTOOS OR SEMI-PERMANENT TATTOOS

TECHNICAL FIELD

The present invention relates to a tattooing apparatus, which can adjust a concentration of a staining solution for tattoo or semipermanent makeup, and more particularly, to a tattooing apparatus, which repeatedly inserts and takes out a tattoo needle into and from a skin while applying the staining solution for tattoo on the skin for penetrating the staining solution for tattoo into the skin.

BACKGROUND ART

In general, a tattooing apparatus is an apparatus, which represents signs, letters, a pattern or picture, such as figures, on a skin of humans by using a staining solution for tattoo and a tattoo needle.

For convenience of tattoo procedures, a conventional tattooing apparatus is configured, so that the tattoo needle automatically travels back and forth and the staining solution for tattoo rides the tattoo needle down while it travels back and forth. Here, since the tattoo needle moves while sticking at a given depth on the skin, a tattoo of given shape is represented on the skin as a tattoo practitioner intended.

However, there are frequent occasions when the tattoo represents various colors and shadings as well as shapes. For this, in representing the tattoo, it is necessary for the practitioner practitioner to perform the tattoo procedures with changing colors of the tattoo in concentration. In this case, the practitioner practitioner usually adjusts a force of pressing the tattooing apparatus against the skin in the process of performing the tattoo procedure, thereby controlling the concentration of the tattoo (the picture or design, the letters, etc.) to be represented. According to this, when changing the staining solution for tattoo in concentration, the practitioner practitioner requires a high degree of skills. Thus, there was a problem in that in case of the practitioner not well trained, it is difficult for her or him to carry out an operation of uniformly representing the tattoo in various concentrations.

DISCLOSURE

Technical Problem

Exemplary embodiment of the present invention addresses at least the above problems and/or disadvantages and provide at least the advantages described below. Accordingly, an aspect of the present invention is to provide a tattooing apparatus, which can represent a shape of tattoo to be formed on a skin in various concentrations by adjusting an amount of discharging a staining solution for tattoo through a quick and convenient operation.

Another aspect of the present invention is to provide a tattooing apparatus, which can easily adjust a suction amount of a staining solution for tattoo when a storing chamber is filled with the staining solution for tattoo through an outlet of a guide member.

Technical Solution

According to one aspect of an exemplary embodiment of the present invention, there is provided a tattooing apparatus, including a tattoo needle movable back and forth to a skin to allow a staining solution for tattoo contained in the apparatus to penetrate into the skin and thus to get a tattoo, and a chamber pressure adjusting member to adjust a degree of opening and closing an inlet of a storing chamber in which the staining solution for tattoo is stored, thus to adjust a pressure in the storing chamber.

The chamber pressure adjusting member may rotate in a first direction and a second direction opposite to the first direction to adjust the degree of opening and closing the inlet of the storing chamber. In this case, the chamber pressure adjusting member may have an anti-sliding protrusion formed along an outer circumference thereof.

A stroke of the tattoo needle may be selectively changed to adjust a depth of the tattoo needle sticking on the skin.

According to another aspect of an exemplary embodiment of the present invention, there is provided a tattooing apparatus, including a main body having a power source therein; a cap part detachably coupled to a side of the main body and having a first inlet formed on a circumferential surface thereof and a first storing chamber provided therein to communicate with the first inlet; a tattoo needle support disposed in the first storing chamber of the cap part to be movable back and forth and a tattoo needle disposed on a side thereof; a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof; and a chamber pressure adjusting member coupled to a portion of the cap part to adjust a degree of opening and closing the first inlet of the cap part and thus to allow a pressure in the single storing chamber to be adjusted.

The cap part preferably has a cylindrical shape, and the chamber pressure adjusting member preferably has a ring shape and is preferably rotatably disposed to a portion on which the first inlet is formed.

The chamber pressure adjusting member may have a third inlet formed in a size corresponding to the first inlet. The chamber pressure adjusting member preferably has an anti-sliding protrusion formed along an outer circumference thereof.

The guide member may have a flange portion to prevent the chamber pressure adjusting member from being released from the cap part.

The tattooing apparatus may further include a connection rod detachably snapped and coupled with the tattoo needle support to transmit a power generated from the power source of the main body to the tattoo needle support, and the tattoo needle support may selectively change a stroke according to an angle coupled with the connection rod to adjust a depth of the tattoo needle sticking on the skin.

The connection rod may have first and second coupling holes selectively snapped and coupled with at least one coupling protrusion formed on the tattoo needle support, and one of the first and second coupling holes may be coupled with the at least one coupling protrusion while having a space thereto, so that the tattoo needle support travels back and forth in a stroke shorter than a forward and rearward shuttle distance of the connection rod.

According to other aspect of an exemplary embodiment of the present invention, there is provided a tattooing apparatus, including a main body having a power source therein; a cap part in a form of cylinder detachably coupled to a side of the main body and having a first inlet formed on a circumferential surface thereof and a first storing chamber provided therein to communicate with the first inlet; a tattoo needle support disposed in the first storing chamber of the cap part to be movable back and forth and a tattoo needle disposed on a side thereof; and a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof, wherein the guide member is rotatably coupled to the cap part to adjust a degree of opening and closing the first inlet of the cap part and thus to allow a pressure in the single storing chamber to be adjusted.

The guide member may have a second inlet formed in a size corresponding to the first inlet at the one side thereof inserted in the cap part. The guide member preferably has an anti-sliding protrusion formed along an outer circumference of the other side thereof, which is not inserted in the cap part.

The guide member may have a flange portion formed along an outer circumference thereof, and the anti-sliding protrusion may be formed on the outer circumference of the flange portion.

To prevent the staining solution for tattoo stored in the single storing chamber from being leaked, a sealing member may be disposed between the cap part and the guide member.

The tattooing apparatus may further include a connection rod detachably snapped and coupled with the tattoo needle support to transmit a power generated from the power source of the main body to the tattoo needle support, and the tattoo needle support may selectively change a stroke according to an angle coupled with the connection rod to adjust a depth of the tattoo needle sticking on the skin.

The connection rod may have first and second coupling holes selectively snapped and coupled with at least one coupling protrusion formed on the tattoo needle support, and one of the first and second coupling holes may be coupled with the at least one coupling protrusion while having a space thereto, so that the tattoo needle support travels back and forth in a stroke shorter than a forward and rearward shuttle distance of the connection rod.

Advantageous Effects

According to the aspects of the exemplary embodiment of the present invention, there is an advantage in that a concentration of the staining solution for tattoo can be changed by adjusting the amount of discharging the staining solution for tattoo and the stroke of the tattoo needle support through a simple operation of rotating the chamber pressure adjusting member or the guide member at an angle of predetermined degrees in one direction and the other direction opposite thereto.

Also, there is an advantage in that the staining solution for tattoo can be conveniently filled through the outlet of the guide member.

BEST MODE

Hereinafter, a configuration of an tattooing apparatus according to exemplary embodiments of the present invention will now be described in greater detail with reference to the accompanying drawings.

Figure 1:
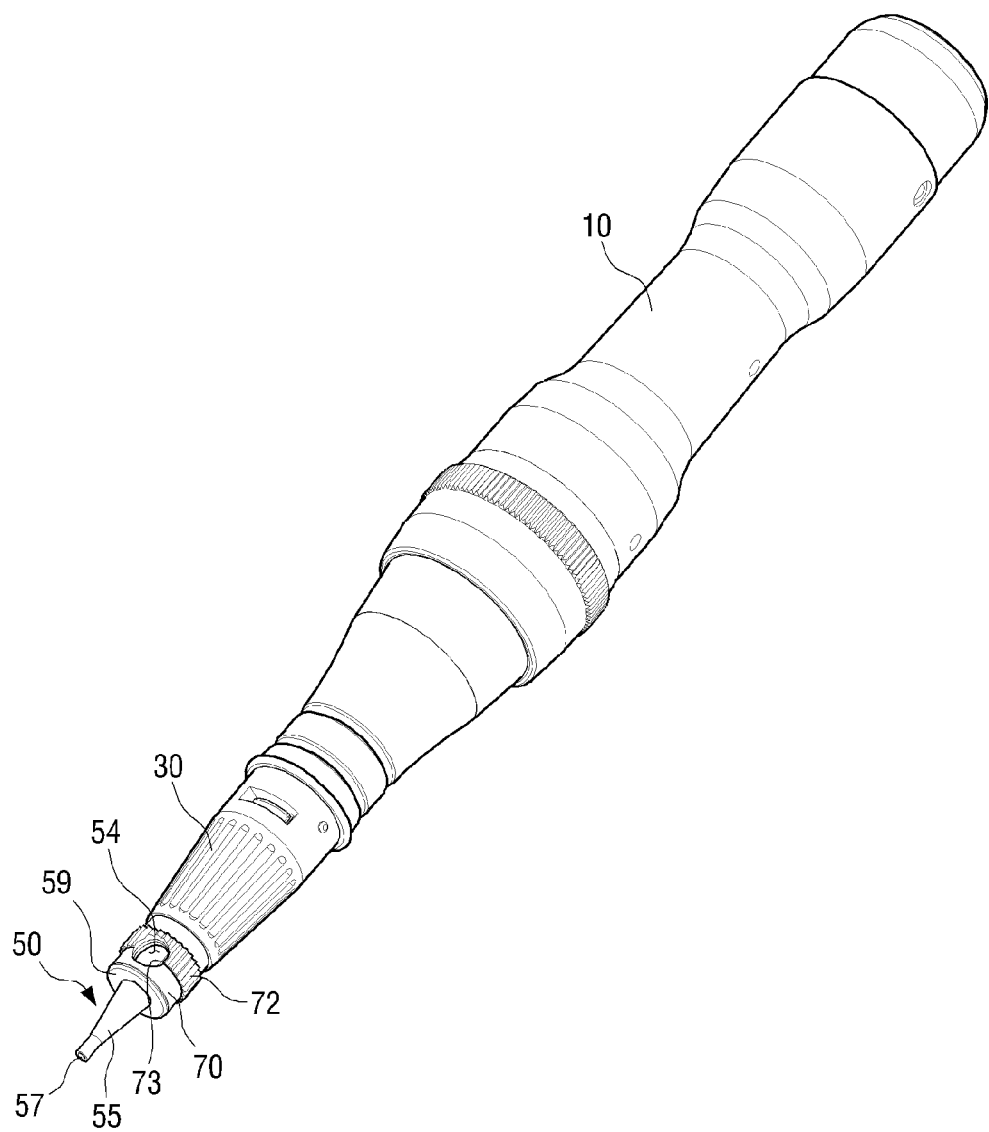
FIG. 1 is a perspective view showing an tattooing apparatus according to a first exemplary embodiment of the present invention.

Referring to FIG. 1, an tattooing apparatus according to a first exemplary embodiment of the present invention includes a main body 10, a cap part 30, a guide member 50, and a chamber pressure adjusting member 70.

The main body 10 is formed to have such a length that a user can easily grasp it. In the main body 10 is installed a power transmitting structure for driving a tattoo needle support 35 (see FIG. 3) to travel back and forth in a straight line.

Figure 2:
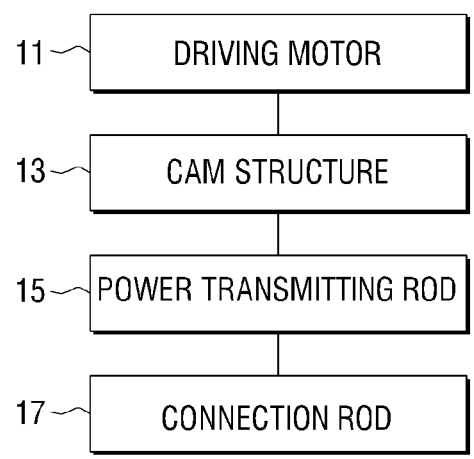
FIG. 2 is a perspective view showing a power transmitting structure, which is installed in a main body of the tattooing apparatus according to the first exemplary embodiment of the present invention.

As shown in FIG. 2, the power transmitting structure includes a driving motor 11, a cam structure 13, a power transmitting rod 15, a connection rod 17 and a hub 18.

The driving motor 11 functions as a power source to receive a power from the outside and to drive the tattoo needle support 35. The cam structure 13 converts a rotating movement of the driving motor 11 into a linear shuttle or reciprocating movement and is connected to a rotary shaft of the driving motor 11. The power transmitting rod 15 transmits the power, that is, a driving force, converted into the linear shuttle movement by the cam structure 13 to the connection rod 17.

Figure 3:
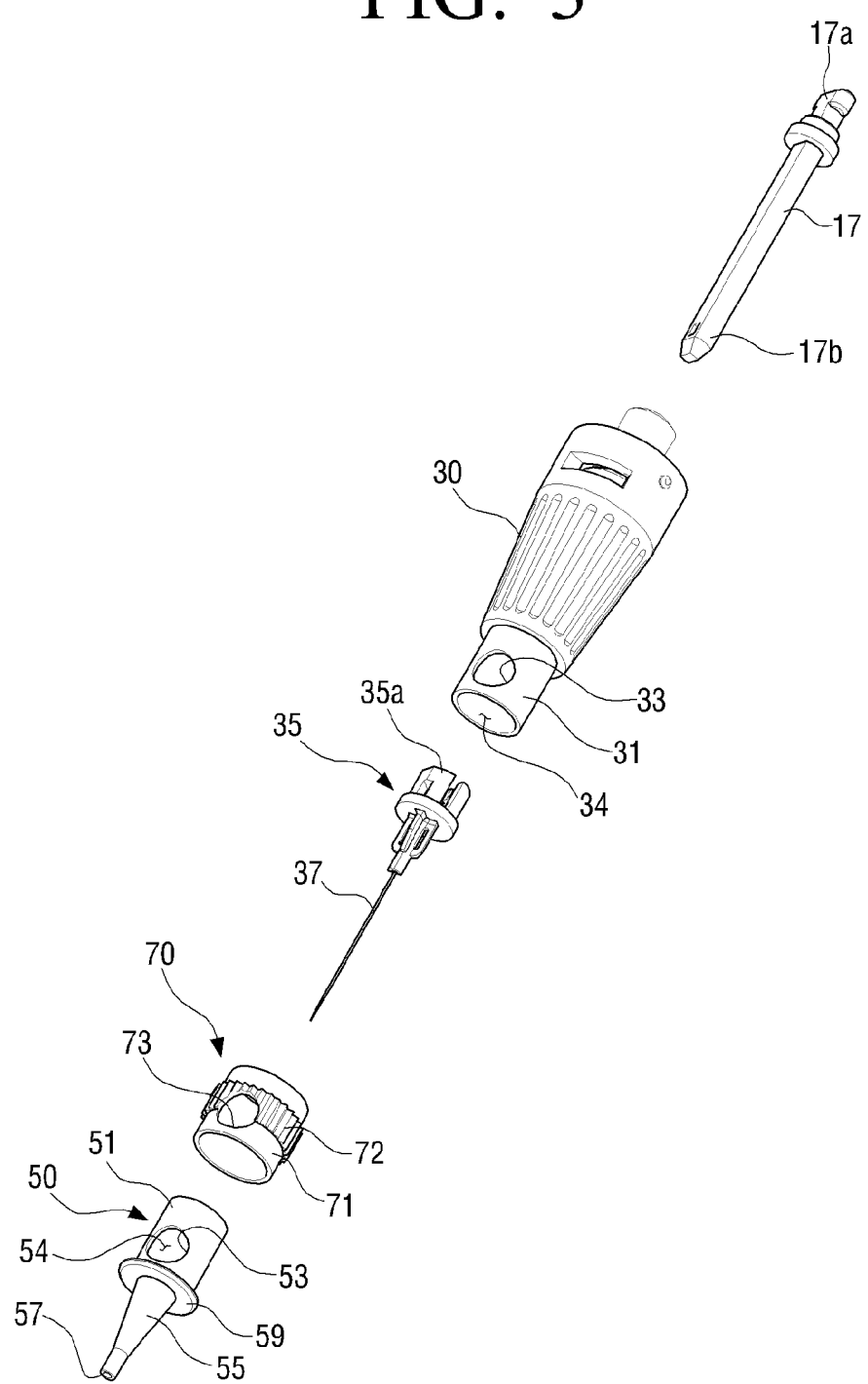
FIG. 3 is an exploded perspective view showing a pressure adjusting configuration, which is installed in a cap part.

As shown in FIG. 3, the connection rod 17 at one end 17a thereof is detachably coupled to the power transmitting rod 15. Further, the connection rod 17 at the other end 17b thereof is snapped and coupled to a rear end 35a of the tattoo needle support 35. According to this, the power transmitting rod 15 and the tattoo needle support 35 are detachably coupled to each other.

The hub 18 is coupled with the connection rod 17, so that the connection rod 17 can penetrate the hub 18 and travel back and forth therein. The hub 18 prevents the connection rod 17 from rotating when it travels back and forth. Moreover, as shown in FIG. 3, the hub 18 has a protruded coupling portion 18a coupled in a recessed groove 30a of the cap part 30. According to this, even if the tattooing apparatus according to the present exemplary embodiment is positioned to stand upside down, a leakage of a staining solution for tattoo from a chamber C to be described later is prevented.

Figure 5:
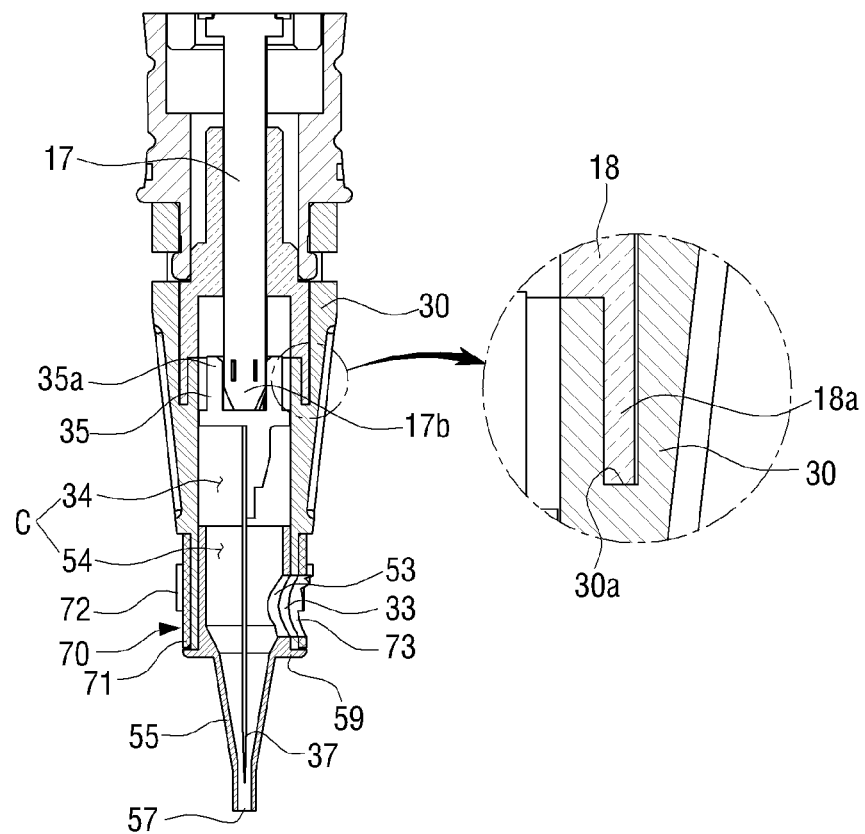
FIG. 5 is a cross-sectional view taken along line V-V shown in FIG. 4.

As shown in FIGS. 3 and 5, the cap part 30 includes a coupling portion 31, a first inlet 33, a first storing chamber 34, a tattoo needle support 35, and a tattoo needle 37. The cap part 30 at a rear end thereof is detachably coupled to an end of the main body 10 (see FIG. 1).

The coupling portion 31 is formed in the form of approximately cylinder and at a circumferential surface thereof has the first inlet 33, which can put in the staining solution for tattoo.

The first storing chamber 34 is provided inside the cap part 30 to store the staining solution for tattoo put in through the first inlet 33. In this case, the tattoo needle support 35 is disposed in the first storing chamber 34 to travel back and forth or reciprocate therein.

The tattoo needle support 35 forces the staining solution for tattoo stored in the first storing chamber 34 to discharge by predetermined amounts to an outlet 57 of the guide member 50 while reciprocating in the first storing chamber 34.

The tattoo needle 37 is coupled to a front end of the tattoo needle support 35. As the tattoo needle support 35 reciprocates in the first storing chamber 34, the tattoo needle 37 repeats the shuttle or reciprocating movement where a front end thereof projects to the outside through the outlet 57 of the guide member 50 and then goes into the guide member 50 again.

According to such a reciprocating movement, the tattoo needle 37 allows the staining solution for tattoo to penetrate into a skin thus to tattoo the skin while repeating the movement where it is inserted to a predetermined depth into and then drawn out from the skin.

The guide member 50 include an inserting portion 51, a second inlet 53, a second storing chamber 54, a front end 55, and a flange portion 59.

The inserting portion 51 is located at a rear end of the guide member 50, and formed in the form of approximately cylinder. The inserting portion 51 is detachably inserted into the coupling portion 31 of the cap part 30. At this time, the inserting portion 51 and the coupling portion 31 are coupled in a pressed state to each other not to leak the staining solution for tattoo through therebetween.

The second inlet 53 is formed on a circumferential surface of the inserting portion 51, so that it is equal or a little larger than the first inlet 33 formed on the coupling portion 31. In this case, when coupled in the coupling portion 31, the inserting portion 51 is preferably coupled, so that it is set in a position where the first and the second inlets 33 and 35 coincide with each other.

The second storing chamber 54 is formed inside the guide member 50, and as shown in FIG. 5, when the inserting portion 51 of the guide member 50 is coupled in the coupling portion 31 of the cap part 30, forms a single storing chamber C together with the first storing chamber 34 of the cap part 30 while communicating therewith.

The front end 55, which has approximately cone shape, is formed on and extended from a side of the inserting portion 51. Further, the front end 55 at a side, that is, a tip thereof has an outlet 57 through which the staining solution for tattoo stored in the single storing chamber C is discharged. In this case, due to the reciprocating movement of the tattoo needle support 35, the tattoo needle 37 repeatedly passes through the outlet 57, and the outlet 57 is formed to have a diameter a little larger than that of the tattoo needle 37 to allow the staining solution for tattoo to pass therethrough with the tattoo needle 37 when it passes therethrough.

The flange part 59 is formed and projected along a border between the inserting portion 51 and the front end 55, and prevents the chamber pressure adjusting member 70 from being released from the coupling portion 31 of the cap part 30.

The chamber pressure adjusting member 70 includes a body 71 in the form of approximately ring and a third inlet 73.

The body 71 is sliding-rotatably coupled on an outer circumferential surface of the coupling portion 31 of the cap part 30, and has an anti-sliding protrusion 72 formed on an outer circumference thereof to allow the user to easily rotate the chamber pressure adjusting member 70.

The third inlet 73 is formed in a size approximately corresponding to the first inlet 33 of the cap part 30. On the other hand, if putting in the staining solution for tattoo into the storing chamber C, the body 71 is rotated in one direction or the other direction opposite thereto, so that it is set in a state where a position of the third inlet 73 is in accord with that of the first inlet 33.

An operation of the tattooing apparatus according to the first embodiment of the present invention constructed as described above will be explained with reference to FIGS. 4 to 6.

When the tattooing apparatus is turned on, the driving motor 11 is operated and a power, that is, a driving force transmitted from the driving motor 11 to the cam structure 13 is converted from a rotating movement to a linear shuttle or reciprocating movement. The driving force converted to the linear shuttle movement as described above is transmitted to the tattoo needle support 35 through the power transmitting rod 15 and the connection rod 17 and thus the tattoo needle support 35 is traveled back and forth at a high speed in the storing chamber C.

In this case, according to the shuttle movement of high speed of the tattoo needle support 35, a pressure lower than the atmospheric pressure is formed in the storing chamber C, and in such a state, the staining solution for tattoo stored in the storing chamber C is discharged through the outlet 57 with stuck to an outer circumferential surface of the tattoo needle 37.

According to this, the staining solution for tattoo is naturally penetrated into the skin by the tattoo needle 37, which is inserted into the skin through the outlet 57.

Figure 4:
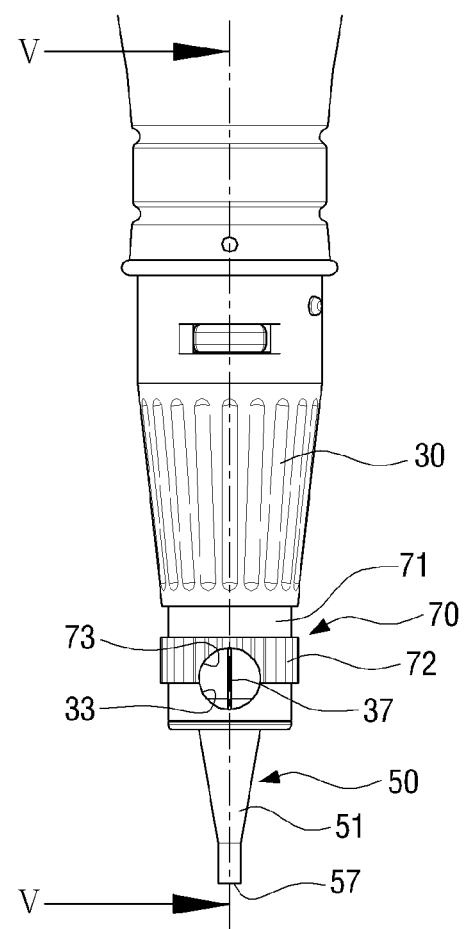
FIG. 4 is a schematic view showing a state where an inlet for putting in a staining solution is completely opened.
Figure 6:
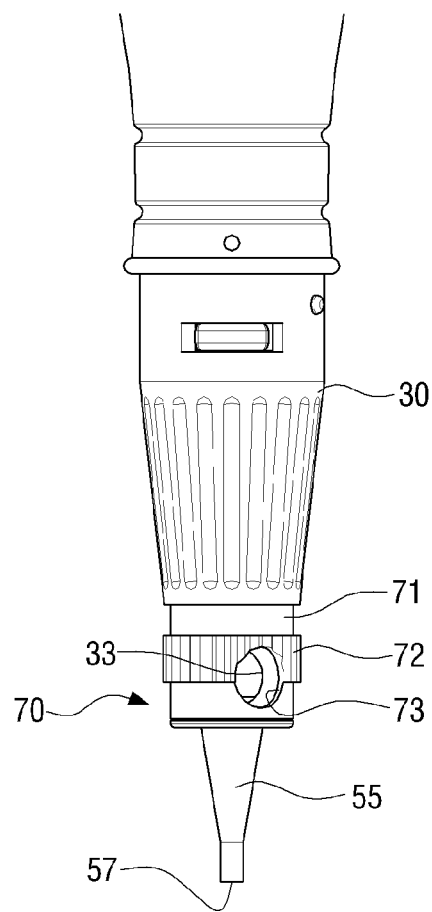
FIG. 6 is a schematic view showing a state where a first inlet of the cap part is partly doused up by a chamber pressure adjusting member.

According to the tattooing apparatus of the first embodiment of the present invention as described above, if adjusting a color of tattoo light in the process of tattooing, as shown in FIG. 6, the chamber pressure adjusting member 70 is rotated at an angle of predetermined degrees in one direction to partly close up the first inlet 33, which is in a completely opened state, as shown in FIG. 4.

When the first inlet 33 is partly closed up, a pressure in the storing chamber C become lower as compared with that when the first inlet 33 is in the completely opened state. According to this, a discharging amount of the staining solution for tattoo discharged through the outlet 57 is reduced and after all, the tattoo formed on the skin is represented at a lower concentration.

As described above, since the tattooing apparatus of the first embodiment is free to represent a brightness or shading of the tattoo, a tattoo practitioner can easily adjust the concentration of the staining solution for tattoo in the process of performing the tattoo procedure even if she or he has not been well trained.

On the other hand, if the staining solution for tattoo is used up and thereby the storing chamber C is vacated, to fill the storing chamber C with the staining solution for tattoo again, the driving motor 11 is driven in a state where the front end 55 of the guide member 50 is partly soaked in the staining solution for tattoo. According to this, the tattoo needle support 35 pumps the staining solution for tattoo into the storing chamber C through the outlet 57, thus to fill the storing chamber C with the staining solution, while moving back and forth. Through this, the storing chamber C in the tattooing apparatus of the first embodiment can be easily filled with the staining solution for tattoo even without using the first to third inlets 33, 53, and 73.

At this time, the chamber pressure adjusting member 70 in the tattooing apparatus of the first embodiment is rotated to adjust the degree of opening and closing the first inlet 33, thereby allowing an amount of pumping the staining solution for tattoo to be adjusted according to a viscosity thereof. In other words, in the tattooing apparatus of the first embodiment, the more the amount of opening the first inlet 33 is reduced, the more the amount of pumping the staining solution for tattoo is increased.

Figure 7:
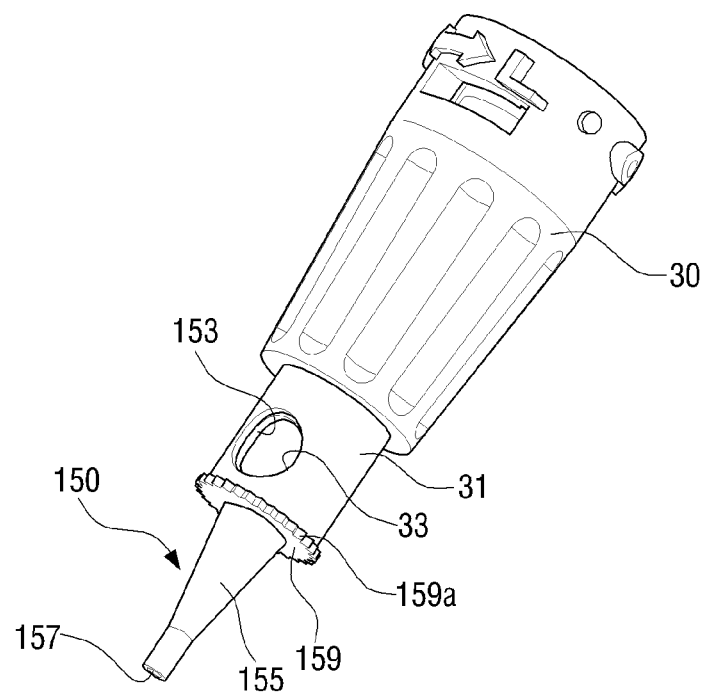
FIG. 7 is an assembled perspective view showing a cap part and a guide member of an tattooing apparatus according to a second exemplary embodiment of the present invention.
Figure 8:
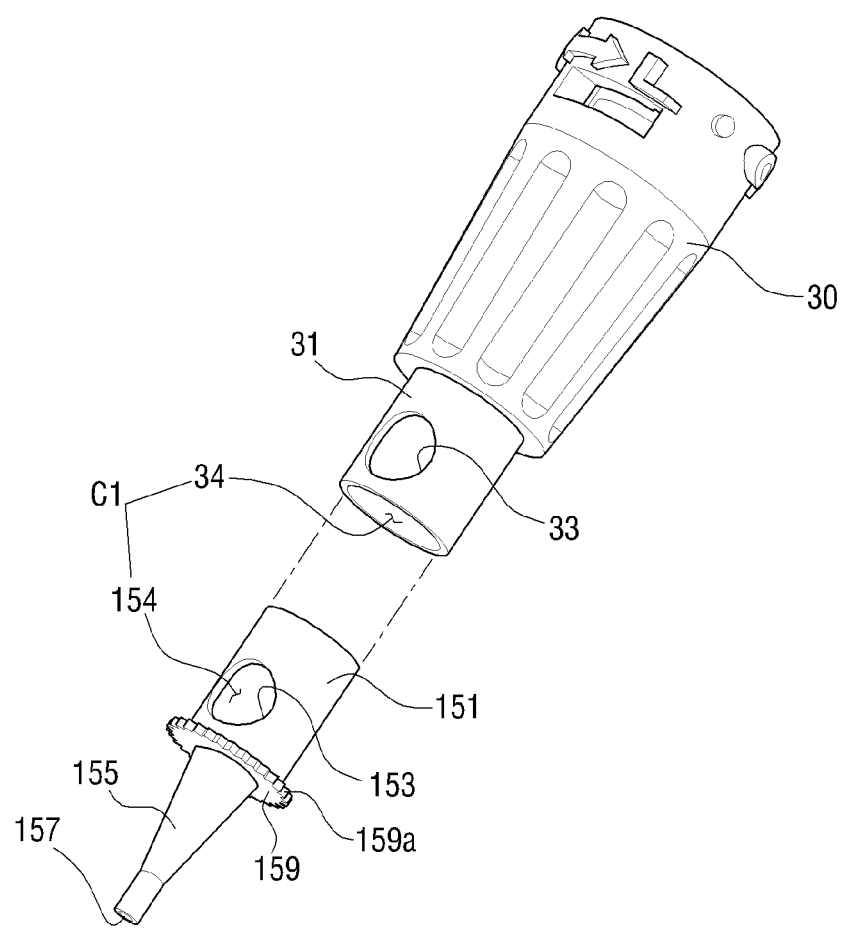
FIG. 8 is an exploded perspective view showing the cap part and the guide member of the tattooing apparatus according to the second exemplary embodiment of the present invention.

Hereinafter, a tattooing apparatus according to a second embodiment of the present invention will be explained with reference to FIGS. 7 and 8. The tattooing apparatus of the second embodiment has almost the same configurations as those of the tattooing apparatus of the first embodiment, except that a guide member 150 is configured to double as the chamber pressure adjusting member 70 in the tattooing apparatus of the first embodiment. On this account, the tattooing apparatus of the second embodiment can omit the chamber pressure adjusting member 70 in the tattooing apparatus of the first embodiment. Here, only different configurations from the first embodiment except the same configurations as the first embodiment will be explained.

The guide member 150 is configured similar with the first embodiment. In other words, the guide member 150 includes an inserting portion 151 inserted in the coupling portion 31 of the cap part 30, a second inlet 153 having the approximately same size as the first inlet 33, a second storing chamber 154 forming a single storing chamber C1 together with the first storing chamber 34, a front end 155 having an outlet 157 and a flange portion 159.

The flange portion 159 is formed and projected along a border between the inserting portion 151 and the front end 155, and has an anti-sliding protrusion 159a formed on an outer circumference thereof to allow the user to easily rotate the guide member 150 in a state where it is inserted in the coupling portion 31. In this case, a sealing member (not shown) is preferably disposed between the coupling portion 31 of the cap part 30 and the inserting portion 151 of the guide member 150 to prevent the staining solution for tattoo stored in the storing chamber C1 from being leaked.

According to the tattooing apparatus of the second embodiment configured as described above, to adjust a pressure in the storing chamber C1, the guide member 150 is rotated in one direction or the other direction opposite thereto in a state where the flange portion 159 is grasped by the user, thereby setting the degree of opening and closing the first inlet 33. According to this, the tattooing apparatus of the second embodiment can adjust the concentration of the staining solution for tattoo through an adjustment in the discharging amount thereof.

Also, if filling the storing chamber c1 with the staining solution for tattoo through the outlet 157, the tattooing apparatus of the second embodiment can adjust a suction amount of the staining solution for tattoo by rotating the guide member 150.

Figure 9:
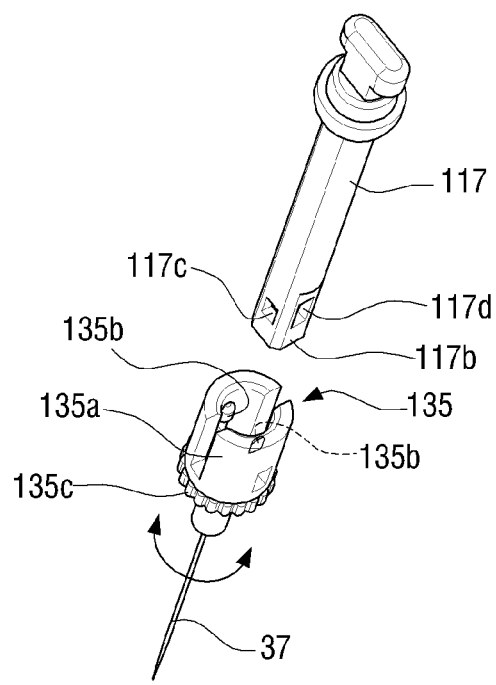
FIG. 9 is an exploded perspective view showing another example of a tattoo needle support and a connection rod of an tattooing apparatus according to a third exemplary embodiment of the present invention.

Hereinafter, a tattooing apparatus according to a third embodiment of the present invention will be explained with reference to FIGS. 9 to 11. The tattooing apparatus of the third embodiment has a structure for adjusting a stroke of a tattoo needle support 135, which is supplementally applied to the first embodiment or the second embodiment.

Accordingly, in the tattooing apparatus of the third embodiment, configurations on the tattoo needle support 135 and a connection rod 117 are different from those in the first embodiment or the second embodiment. Thus, since the tattooing apparatus of the third embodiment has almost the same configurations as those of the tattooing apparatus of the first embodiment or/and the second embodiment, only different configurations from the first embodiment or/and the second embodiment except the same configurations as the first embodiment or/and the second embodiment will be explained.

The connection rod 117 has a pair of first and second coupling holes 117c and 117d formed along a longitudinal direction thereof at a portion 117b, which is inserted in a rear end 135a of the tattoo needle support 135. In this case, the second coupling hole 117d is formed to have a length longer than the first coupling hole 117c.

The tattoo needle support 135 has a pair of coupling protrusions 135b formed at positions facing each other on an inner circumferential surface of the rear end 135a. The pair of coupling protrusions 135b are selectively snapped and coupled to the first and the second coupling holes 117c and 117d when the tattoo needle support 135 is rotated in one direction or the other direction opposite thereto at an angle of predetermined degrees. In other words, the coupling protrusions 135b are selectively coupled to the first and the second coupling holes 117c and 117d according to an angle at which the tattoo needle support 135 is connected with the connection rod 117.

Also, the tattoo needle support 135 has a plurality of anti-sliding protrusions 135c continuously formed along an outer circumference thereof.

Figure 10:
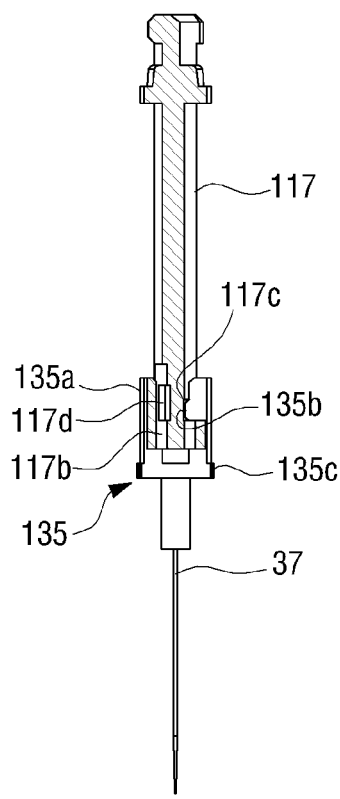
FIGS. 10 and 11 are cross-sectional views showing two modes for adjusting a stroke of the tattoo needle support according to a position of the tattoo needle support.

According to this, as shown in FIG. 10, if the tattooing apparatus of the third embodiment performs the tattoo procedure in a state where the coupling protrusion 135b of the tattoo needle support 135 is snapped and coupled to the first coupling hole 117c, the tattoo needle support 135 is moved in a stroke equal to a forward and rearward moving distance of the connection rod 117.

Figure 11:
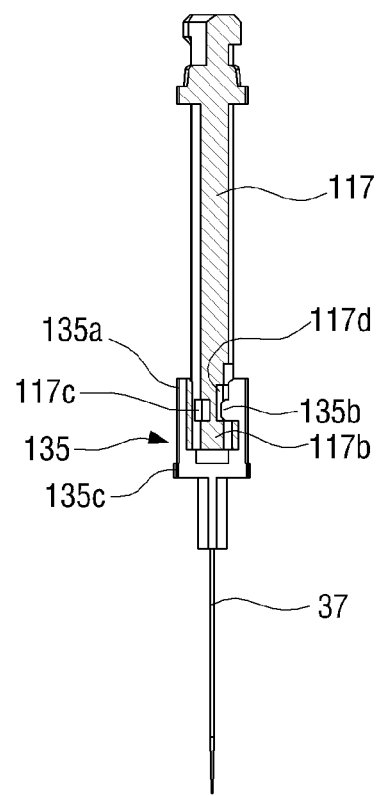

On the other hand, as shown in FIG. 11, if the tattooing apparatus of the third embodiment performs the tattoo procedure in a state where the tattoo needle support 135 is rotated to allow the coupling protrusion 135b to be snapped and coupled to the second coupling hole 117d, the tattoo needle support 135 is moved in a stroke shorter than the forward and rearward moving distance of the connection rod 117. This change is caused by a space generated between the coupling protrusion 135 and the second coupling hole 117d when the connection rod 117 moves back and forth.

As described above, if the coupling protrusion 135b is snapped and coupled in the second coupling hole 117d, the stroke of the tattoo needle support 135 becomes shorter and thus the tattoo needle 37 is not deeply inserted into the skin and the discharging amount of the staining solution for tattoo is also reduced. As a result, since the staining solution for tattoo discharged from the storing chamber C is not deeply penetrated into the skin, it can be set at a lower concentration.

In this case, if the tattoo needle support 135 is adjusted together with the members 70 and 150 for adjusting the chamber pressure of the first and the second embodiments, the concentration of the staining solution for tattoo can be more finely controlled.

Although representative embodiment of the present invention has been shown and described in order to exemplify the principle of the present invention, the present invention is not limited to the specific exemplary embodiment. It will be understood that various modifications and changes can be made by one skilled in the art without departing from the spirit and scope of the invention as defined by the appended claims. Therefore, it shall be considered that such modifications, changes and equivalents thereof are all included within the scope of the present invention.

INDUSTRIAL APPLICABILITY

The tattooing apparatus according to the present invention, as an apparatus that repeatedly inserts and takes out the tattoo needle into and from the skin while applying the staining solution for tattoo on the skin for penetrating the staining solution for tattoo into the skin, can be effectively used in representing the concentration of the tattoo in various ways.

The invention claimed is:

1. A tattooing apparatus, comprising:
a cap part having a first inlet formed on a circumferential surface thereof and a first storing chamber provided therein to communicate with the first inlet;
a tattoo needle support disposed in the first storing chamber of the cap part to be movable back and forth and having a tattoo needle disposed on a side thereof;
a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof; and
a chamber pressure adjusting member coupled to a portion of the cap part that opens and closes the first inlet to adjust a pressure in the single storing chamber.

2. The tattooing apparatus as claimed in claim 1, wherein the chamber pressure adjusting member rotates in a first direction to open the inlet and rotates in a second direction opposite to the first direction to close the inlet.

3. The tattooing apparatus as claimed in claim 2, wherein the chamber pressure adjusting member comprises an anti-sliding protrusion formed along an outer circumference of the chamber pressure adjusting member.

4. A tattooing apparatus, comprising:
a cap part having a first inlet formed on a circumferential surface thereof and a first storing chamber provided therein to communicate with the first inlet;
a tattoo needle support disposed in the first storing chamber of the cap part to be movable back and forth and a tattoo needle disposed on a side thereof; and
a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof,
wherein the guide member is rotatably coupled to the cap part to open and close the first inlet and adjust a pressure in the single storing chamber.

5. A tattooing apparatus, comprising:
a main body having a power source therein;
a cap part detachably coupled to a side of the main body and having a first inlet formed on a circumferential surface thereof and a first storing chamber provided therein to communicate with the first inlet;
a tattoo needle support disposed in the first storing chamber of the cap part to be movable back and forth and having a tattoo needle disposed on a side thereof;
a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof; and
a chamber pressure adjusting member coupled to a portion of the cap part that opens and closes the first inlet to adjust a pressure in the single storing chamber.

6. The tattooing apparatus as claimed in claim 5, wherein the cap part has a cylindrical shape, and the chamber pressure adjusting member has a ring shape and is rotatably disposed to a portion on which the first inlet is formed.

7. The tattooing apparatus as claimed in claim 6, wherein the chamber pressure adjusting member comprises a second inlet formed in a size corresponding to the first inlet.

8. The tattooing apparatus as claimed in claim 5, wherein the chamber pressure adjusting member comprises an anti-sliding protrusion formed along an outer circumference thereof.

9. The tattooing apparatus as claimed in claim 6, wherein the guide member comprises a flange portion to prevent the chamber pressure adjusting member from being released from the cap part.

10. The tattooing apparatus as claimed in claim 5, further comprising:
a connection rod detachably snapped and coupled with the tattoo needle support to transmit a power generated from the power source of the main body to the tattoo needle support,
wherein the tattoo needle support selectively changes a stroke according to an angle coupled with the connection rod to adjust a depth of the tattoo needle sticking in the skin.

11. The tattooing apparatus as claimed in claim 10,
wherein the connection rod comprises first and second coupling holes selectively snapped and coupled with at least one coupling protrusion formed on the tattoo needle support, and
wherein one of the first and second coupling holes is coupled with the at least one coupling protrusion while having a space thereto, so that the tattoo needle support travels back and forth in a stroke shorter than a forward and rearward shuttle distance of the connection rod.

12. A tattooing apparatus, comprising:
a main body having a power source therein;
a cap part in a form of cylinder detachably coupled to a side of the main body and having a first inlet formed on a circumferential surface thereof and a first storing chamber provided therein to communicate with the first inlet;
a tattoo needle support disposed in the first storing chamber of the cap part to be movable back and forth and a tattoo needle disposed on a side thereof; and
a guide member inserted into and coupled to the cap part at one side thereof and having a second storing chamber provided therein to form a single storing chamber together with the first storing chamber and an outlet for discharging a staining solution for tattoo stored in the single storing chamber formed at the other side thereof,
wherein the guide member is rotatably coupled to the cap part to open and close the first inlet and adjust a pressure in the single storing chamber.

13. The tattooing apparatus as claimed in claim 12, wherein the guide member comprises a second inlet formed in a size corresponding to the first inlet at the one side thereof inserted in the cap part.

14. The tattooing apparatus as claimed in claim 12, wherein the guide member comprises an anti-sliding, protrusion formed along an outer circumference of the other side thereof, which is not inserted in the cap part.

15. The tattooing apparatus as claimed in claim 12, wherein the guide member comprises a flange portion formed along an outer circumference thereof, and an anti-sliding protrusion is formed on the outer circumference of the flange portion.

16. The tattooing apparatus as claimed in claim 12, wherein a sealing member is disposed between the cap part and the guide member to prevent the staining solution for tattoo stored in the single storing chamber from being leaked.

17. The tattooing apparatus as claimed in claim 12, further comprising:
   a connection rod detachably snapped and coupled with the tattoo needle support to transmit a power generated from the power source of the main body to the tattoo needle support, and
   wherein the tattoo needle support selectively changes a stroke according to an angle coupled with the connection rod to adjust a depth of the tattoo needle sticking in the skin.

18. The tattooing apparatus as claimed in claim 17,
   wherein the connection rod comprises first and second coupling holes selectively snapped and coupled with at least one coupling protrusion formed on the tattoo needle support, and
   wherein one of the first and second coupling holes is coupled with the at least one coupling protrusion while having a space thereto, so that the tattoo needle support travels back and forth in a stroke shorter than a forward and rearward shuttle distance of the connection rod.

\* \* \* \* \*